(12) United States Patent
Nishimura et al.

(10) Patent No.: US 6,566,551 B2
(45) Date of Patent: May 20, 2003

(54) METHOD FOR PREVENTING EFFLUENT GAS PIPE FROM BLOCKING

(75) Inventors: Takeshi Nishimura, Hyogo (JP); Yukihiro Matsumoto, Hyogo (JP); Sei Nakahara, Hyogo (JP); Misao Inada, Hyogo (JP); Harunori Hirao, Hyogo (JP); Mamoru Takamura, Hyogo (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/724,468

(22) Filed: Nov. 29, 2000

(65) Prior Publication Data

US 2001/0003783 A1 Jun. 14, 2001

(30) Foreign Application Priority Data

Dec. 2, 1999 (JP) .......................... 11-343442
Dec. 6, 1999 (JP) .......................... 11-345673

(51) Int. Cl.$^7$ .......................... C07C 51/16
(52) U.S. Cl. .................. 562/542; 562/549; 562/518; 562/532
(58) Field of Search ................ 562/542, 549, 562/518, 532

(56) References Cited

U.S. PATENT DOCUMENTS 4,256,675 A * 3/1981 Vanderspurt et al.
5,780,679 A * 7/1998 Egly et al.
5,785,821 A 7/1998 Sakamoto et al. ............ 203/57

\* cited by examiner

*Primary Examiner*—Paul F. Shaver
(74) *Attorney, Agent, or Firm*—Mathews, Collins, Shepherd & McKay, P.A.

(57) ABSTRACT

For use in a process for the production of (meth)acrylic acid comprising at least a step for the reaction of (meth)acrylic acid by catalytic gas phase oxidation and a step for the absorption thereof, a method for preventing an effluent gas pipe from blocking is disclosed, which method is characterized by causing part or the whole of the gas discharged from the step for absorption, while being circulated via the effluent gas pipe to the step for the reaction or being discarded, to be subjected to temperature elevation and application of pressure and/or mist separation. Particularly by setting the temperature of the waste gas from the absorption column at a level in the range of 30–70° C., it is made possible to decrease the contents of water, low boiling substances, and subliming substances entrained by the waste gas and, coupled with the temperature elevation and the application of pressure implemented in the effluent gas pipe, attain effective prevention of the interior of the effluent gas pipe from blockage and corrosion.

17 Claims, 2 Drawing Sheets

METHOD FOR PREVENTING EFFLUENT GAS PIPE FROM BLOCKING

BACKGROUND OF THE INVENTION

1. Field of the Invention

This invention, in the production of a (meth)acrylic acid comprising a step of absorbing the (meth)acrylic acid from the reaction gas obtained by the reaction of catalytic gas phase oxidation, relates to a method for preventing an effluent gas pipe from blocking, characterized by subjecting a discharged gas generated during the step of absorption mentioned above to temperature elevation and pressure application during the process of discarding the waste gas or circulating the discharged gas to a reactor used for the catalytic gas phase reaction, a method for preventing an effluent gas pipe from blocking, characterized by separating and removing mist before and/or after the temperature elevation, and a method for the production of a (meth)acrylic acid, characterized by subjecting a discharged gas to temperature elevation and pressure application or putting the discharged gas to cyclic use during a step of reaction after the removal of mist.

2. Description of the Related Art

Such polymerizable substances as acrylic acid and methacrylic acid are raw materials for commercial production and are chemical substances which are produced in large amounts in a plant of a large scale. Generally, compounds often pass through various steps of absorption and purification for the purpose of obtaining products of high purity and generate waste gases at such steps.

When propylene, propane, isobutylene, and methacrolein are subjected to catalytic gas phase oxidation with a molecular oxygen-containing gas in the presence of an oxidizing catalyst, for example, the oxidation forms in addition to the (meth)acrylic acid, i.e. the target product, such substances as aldehyde which have lower boiling points than the target product, such carboxylic acids as terephthalic acid and benzoic acid which have higher boiling points than the target product, and tarry substances as by-products. For this reason, the mixed gas consequently obtained is led to a (meth)acrylic acid absorbing column and allowed to contact a (meth)acrylic acid absorbent with a view to attaining absorption and consequently obtaining a solution containing the (meth)acrylic acid and other by-products. This solution is distilled to separate the (meth)acrylic acid as a refined product. Particularly, in the reaction of catalytic gas phase oxidation of propylene, etc. mentioned above, since the (meth)acrylic acid is produced by supplying to a reactor the raw material gas obtained by combining the propylene, etc. with oxygen gas and an inert gas and adjusting them to a prescribed composition, the gas components, inert gas and oxygen gas are continuously discharged through the reactor and the top of the (meth)acrylic acid absorbing column.

The gas thus discharged can be disposed of as a waste gas through a step of combustion. The official gazette of JP-A-09-157,213, for example, discloses a method for utilizing, though not quite satisfactorily, the gas discharged through the acrylic acid absorbing column by means of recycling the gas to a step for reaction of oxidation.

The operation of leading the (meth)acrylic acid-containing gas obtained by catalytic gas phase oxidation of propylene to the absorbing column and absorbing the gas in a solution as described above is in vogue in the process for the production of (meth)acrylic acid. Then, the practice of recycling the residual gas which is obtained through the top of the absorbing column after the absorption of the solution to a reactor for catalytic gas phase oxidation with a view to being reused as a diluting gas therein or disposing the residual gas as a waste gas is also in vogue.

The discharged gas of this origin, however, entrains such subliming substances as terephthalic acid by-produced by the reaction of catalytic gas phase oxidation, such low-boiling substances as formaldehyde, such inert gases as carbon dioxide and nitrogen gas supplied to the reactor together with the raw material gas, and molecular oxygen and water. When the gas discharged through the (meth)acrylic acid absorbing column is circulated through the effluent gas pipe to the step for reaction of catalytic oxidation, therefore, the low boiling formaldehyde entrained by the waste gas is polycondensed possibly to the extent of blocking the effluent gas pipe.

Further, since the water introduced into the step of reaction and the water used during the step for absorbing (meth)acrylic acid are effluxed as the discharged gas during the step for this absorption, this discharged gas entails such hindrances as adhering to the effluent gas pipe and corroding the compressor and, particularly when suffered to adhere to the air blower, inducing degradation of the function of air blowing. Thus, the relevant devices need periodic internal inspection, removal of polycondensate, and replacement of corroding units possibly to the extent of obstructing continuous operation.

Meanwhile in the reaction of catalytic gas phase oxidation, since the raw material gas is capable of explosion and combustion, it is preferred to be supplied to the reaction in a composition which falls outside the explosion limits. This mixed gas, therefore, contains an inert gas in a high concentration. When the gas component remaining after the reaction for catalytic gas phase oxidation is released as formed into the ambient air and when the inert gas happens to be carbon dioxide, therefore, this release is naturally improper from the viewpoint of preventing global warming.

SUMMARY OF THE INVENTION

The present inventor, as a result of his diligent study of the gas component discharged from the (meth)acrylic acid absorbing column, has found that the effluent gas pipe can be prevented from blocking by subjecting the discharged gas to temperature elevation and pressure application. This invention has been perfected based on this knowledge. To be specific, the object of the invention mentioned above is accomplished by the following items (1)–(3).

(1) In a process for the production of (meth)acrylic acid comprising at least a step for the reaction of (meth)acrylic acid by catalytic gas phase oxidation and a step for the absorption thereof, a method for preventing an effluent gas pipe from being blocked, characterized by causing part or the whole of the gas discharged from the step of absorption, while being circulated via an effluent gas pipe to the step of reaction or being discarded, to be maintained at the same temperature as the temperature of the gas discharged from the step of absorption or to be elevated to a higher temperature.

(2) In a process for the production of (meth)acrylic acid comprising at least a step for the reaction of (meth)acrylic acid by catalytic gas phase oxidation and a step for the absorption thereof, a method for preventing an effluent gas pipe from being blocked, characterized by causing part or the whole of the gas discharged from the step of absorption, while being circulated via said effluent gas pipe to the step of reaction or being discarded, to be stripped of mist.

(3) A method for the production of (meth)acrylic acid comprising at least a step for the reaction of (meth)acrylic acid by catalytic gas phase oxidation and a step for the absorption the formed acid, characterized by causing part or the whole of the gas discharged from the step of absorption at an outlet temperature of the step in the range of 30–70° C., while being circulated via an effluent gas pipe to the step of reaction or being discarded, to be maintained at the same temperature as the temperature of the gas discharged from the step of absorption or to be heated to a higher temperature and to be pressurized.

By setting the temperature of the gas discharged from the step for absorbing (meth)acrylic acid at a level in a prescribed range according to this invention, it is made possible to adjust the concentrations of water, low boiling substance, and subliming substance contained in the discharged gas in a preferred range and consequently prevent these defiling substances from blocking the effluent gas pipe. Particularly by elevating the temperature of the interior of the effluent gas pipe, the low boiling substance and the subliming substance are enabled to remain in the gaseous state. By moreover securing the linear velocity of the gas at a prescribed level, the effluent gas pipe possibly containing a bent part is prevented from adhesion of water, low boiling substance, and subliming substance and consequently allowed to attain effective prevention of blocking.

Further by setting the temperature of the gas discharged from the step for absorbing (meth)acrylic acid at a level in a prescribed range according to this invention, it is made possible to adjust the contents of the low boiling substance and the subliming substance in the (meth)acrylic acid-containing solution occurring in the absorption column in a preferred range, and consequently prevent the (meth)acrylic acid-containing solution from encountering the blockage caused by such defiling substances in the subsequent step for refining. What is more, since it is made possible to adjust the discharged gas, the low boiling substance and the subliming substance in a preferred range, it can be reused effectively at the step of reaction.

A finned-tube type exchanger or a plate-type exchanger is used particularly effectively for elevating the temperature of the gas in the effluent gas pipe which connects the absorption column to the step of reaction because it permits the temperature to be elevated to the target level in a particularly short period of time.

By stripping the discharged gas from the absorption column of the mist according to this invention, the otherwise possible deposition of scale on the pipes and the devices which are disposed subsequently to the absorption column can be effectively prevented. Consequently, the apparatus for the production of (meth)acrylic acid can be stably operated for a long time.

DETAILED DESCRIPTION OF THE PREFERRED EMBODIMENTS

The first aspect of this invention relates, in the production of (meth)acrylic acid comprising at least a step for the reaction of (meth)acrylic acid by catalytic gas phase oxidation and a step for the absorption thereof, to a method for preventing an effluent gas pipe from blocking, characterized by causing part or the whole of the gas discharged from the step for absorption, while being circulated via the effluent gas pipe to the step for the reaction or being discarded, to be maintained at the same temperature as the temperature of the waste gas from the step for absorption or to be elevated to a higher temperature. The second aspect of this invention relates, in the production of (meth)acrylic acid comprising at least a step for the reaction of (meth)acrylic acid by catalytic gas phase oxidation and a step for the absorption thereof, to a method for preventing an effluent gas pipe from blocking, characterized by causing part or the whole of the gas discharged from the step of absorption, while being circulated via said effluent gas pipe to the step of reaction or being discarded, to be stripped of mist.

The (meth)acrylic acid is generally produced in a large amount by a continuous operation. The pipe for circulating the discharged gas generated at the step for absorption to the step for reaction is long and contains bent parts. Thus, the temperature elevation serves the purpose of maintaining the polymerizable substance in a gaseous state and preventing it from succumbing to polymerization and the application of pressure to the gas component attains the purpose of preventing the gas component from stagnating and precluding the otherwise possible deposition of a polymer, with the result that the water entrained by the gas will be prevented from corroding the apparatus and adhering to the blower mechanism possibly to the extent of degrading the function thereof. By separating and removing the mist from the discharged gas emanating from the absorbing column, it is made possible to attain effective prevention of the deposition of scale on the pipes and the devices and consequently to prevent the effluent gas pipe from being blocked. Now, this invention will be described in detail below.

The step for the reaction of (meth)acrylic acid contemplated by this invention does not need to be particularly discriminated but is only required to be a step for preparing (meth)acrylic acid. It is nevertheless preferred to be a reaction for catalytic gas phase oxidation. The reason for this preference is that the composition of the components of the dischaged gas emanating from th absorption column during the reuse of the waste gas resembles that of the inert gas introduced into the reactor so much as to render easy the adjustment of the pressure and the temperature of the gas.

Specifically, the reaction of catalytic gas phase oxidation is implemented by supplying a molecular oxygen-containing gas and an inert gas in prescribed amounts to propylene, propane, isobutylene, methacrolein, etc. held in a reactor such as a shell-and-tube type reactor in the presence of an oxidizing catalyst. Acrolein is formed by using propylene, for example, and acrylic acid is obtained by further subjecting the acrolein to the reaction of catalytic gas phase oxidation. The step for the reaction contemplated by this invention does not need to be discriminated between the one-stage process which performs these two reactions in one reactor and the two-stage process which performs these reactions in two different reactors. For the conditions involved in the reaction of (meth)acrylic acid such as the raw material gas, oxidizing catalyst, inert gas, oxygen gas, and reaction temperature, all the conditions which are adopted in the known process for the reaction of (meth)acrylic acid are invariably applicable.

As the raw material gas, for example, one member or a mixture of two or more members selected from the group consisting of propylene, propane, isobutylene, t-butanol, and methyl-t-butyl ether may be used. Such raw material component is used in an amount in the range of 1–15 vol. % of the total volume of the raw material gas to be supplied to the reactor. The raw material gas comprises molecular oxygen for the reaction of oxidization at a ratio in the range of 1–3 based on the amount of the raw material and the balance consisting of such inert gases as nitrogen, carbon dioxide and steam.

The reactor to be used for effecting the reaction of catalytic gas phase oxidation does not need to be particularly discriminated. A shell-and-tube type reactor can be advantageously used because it excels in terms of the efficiency of reaction.

For the purpose of producing acrylic acid by subjecting a propylene-containing gas to the reaction of two-stage catalytic gas phase oxidation according to this invention, for example, the oxidizing catalyst which is generally used in the production of acrolein by the reaction of catalytic gas phase oxidation of the raw material gas containing propylene can be used as the former-stage catalyst. The latter-stage catalyst does not need to be particularly restricted, either. The oxidizing catalyst which is generally used in the production of acrylic acid by the gas phase oxidation of the reaction gas chiefly containing the acrolein obtained in the former stage by the process of two-stage catalytic gas phase oxidation can be used.

As concrete examples of the former-stage catalyst, the catalysts represented by the general formula, $Mo_a$—$Bi_b$—$Fe_c$-$A_d$-$B_e$—$C_f$-$D_g$-$O_x$ (wherein Mo, Bi, and Fe respectively represent molybdenum, bismuth, and iron, A represents at least one element selected from the group consisting of nickel and cobalt, B represents at least one element selected from the group consisting of alkali metals and thallium, C represents at least one element selected from the group consisting of phosphorus, niobium, manganese, cerium, tellurium, tungsten, antimony, and lead, D represents at least one element selected from the group consisting of silicon, aluminum, zirconium, and titanium, and O represents oxygen, and a, b, c, d, e, f, g, and x respectively represent the atomic ratios of Mo, Bi, Fe, A, B, C, D, and O which fall respecttively in the ranges of b=0.1–10, c=0.1–10, d=2–20, e=0.001–5, f=0–5, and g=0–30 when a=12 is fixed, and x is a numerical value to be fixed by the states of oxidation of the relevant elements) may be cited. Then, as concrete examples of the latter-stage catalyst, the catalysts represented by the general formula, $Mo_a$—$V_b$—$W_c$—$Cu_d$-$A_e$-$B_f$—$C_g$-$O_x$ (wherein Mo represents molybdenum, V represents vanadium, W represents tungsten, Cu represents copper, A represents at least one element selected from the group consisting of antimony, bismuth, tin, niobium, cobalt, iron, nickel, and chromium, B represents at least one element selected from the group consisting of alkali metals, alkaline earth metals, and thallium, C represents at least one element selected from the group consisting of silicon, aluminum, zirconium, and cerium, and O represents oxygen, a, b, c, d, e, f, g, and x respectively represent the atomic ratios of Mo, V, W, Cu, A, B, C, and O which fall respectively in the ranges of b=2–14, c=0–12, d=0.1–5, e=0–5, f=0–5, g=0–20 when a=12 is fixed, and x is a numerical value to be fixed by the states of oxidation of the relevant elements) may be cited.

As the catalyst to be used when methacrylic acid is obtained by the reaction of two-stage catalytic gas phase oxidation of isobutylene, t-butanol, methyl-t-butyl ether according to this invention, the oxidizing catalyst generally used as the former-stage catalyst in the production of methacrolein by the reaction of gas phase oxidation of the raw material gas containing isobutylene may be adopted. The latter-stage catalyst does not need to be particularly discriminated, either. The oxidizing catalyst which is generally used in the production of acrylic acid by the gas phase oxidation of the reaction gas chiefly containing the acrolein obtained in the former stage by the process of two-stage catalytic gas phase oxidation can be used.

Specifically, the former-stage catalyst fit for use herein is represented by the general formula, $Mo_a$—$W_b$—$Bi_c$—$Fe_d$-$A_e$-$B_f$—$C_g$-$D_h$-$O_x$ (wherein Mo, W, and Bi respectively represent molybdenum, tungsten, and bismuth, Fe represents iron, A represents at least one element selected from the group consisting of nickel and cobalt, B represents at least one element selected from the group consisting of alkali metals, alkaline earth metals, and thallium, C represents at least one element selected from the group consisting of phosphorus, tellurium, antimony, tin, cerium, lead niobium, manganese, and zinc, D represents at least one element selected from the group consisting of silicon, aluminum, titanium, and zirconium, and O represents oxygen, and a, b, c, d, e, f, g, h, and x respectively represent the atomic ratios of Mo, W, Bi, Fe, A, B, C, D, and O which respectively fall in the ranges of b=0–10, c=0.1–10, d=0.1–20, e=2–20, f=0–10, g=0–4, and h=0–30 when a=12 is fixed and x is a numerical value to be determined by the states of oxidation of the relevant elements).

The latter-stage catalyst does not need to be particularly discriminated but is only required to be a catalyst formed of one or more oxides having molybdenum and phosphorus as main components. It is properly formed of a phosphomolybdic acid type heteropoly acid or a metal salt thereof. It is preferred to be represented by the general formula, $Mo_a$—$P_b$-$A_c$-$B_d$—$C_e$-$D_f$-$O_x$ (wherein Mo represents molybdenum, P represent phosphorus, A represents at least one element selected from the group consisting of arsenic, antimony, germanium, bismuth, zirconium, and selenium, B represents at least one element selected from the group consisting of copper, iron, chromium, nickel, manganese, cobalt, tin, silver, zinc, palladium, rhodium, and tellurium, C represents at least one element selected from the group consisting of vanadium, tungsten, and niobium, D represents at least one element selected from the group consisting of alkali metals, alkaline earth metals, and thallium, and O represents oxygen, and a, b, c, d, e, f, and x respectively represent the atomic ratios of Mo, P, A, B, C, D, and O which fall respectively in the ranges of b=0.5–4, c=0–5, d=0–3, e=0–4, f=0.01–4 when a=12 is fixed and x is a numerical value to be determined by the states of oxidation of the relevant elements).

The method for preparation excepting the firing temperature of the catalyst to be used in this invention and the raw materials excepting the molybdenum oxide to be used in mixing and forming the catalyst do not need to be particularly discriminated. The methods and the raw materials which are generally used may be invariably adopted. The shape of the catalyst does not need to be particularly restricted. The catalyst may be in the shape of spheres, circiular pillars, and cylinders, for example. As the method for forming the catalyst, deposition, extrusion molding, and compaction in tablets may be adopted. The catalyst which is obtained by depositing a catalytic substance on a refractory carrier is also useful.

The term "step for absorption of (meth)acrylic acid" refers to the step at which the (meth)acrylic acid contained in the gas obtained at the step for reaction. For the absorption of the (meth)acrylic acid regarding such factors as the composition of the reaction gas, composition of the absorbent, and the temperature of absorption, all the conditions which have been used heretofore in the process for absorbing (meth)acrylic acid may be invariably applicable.

Figure 1:
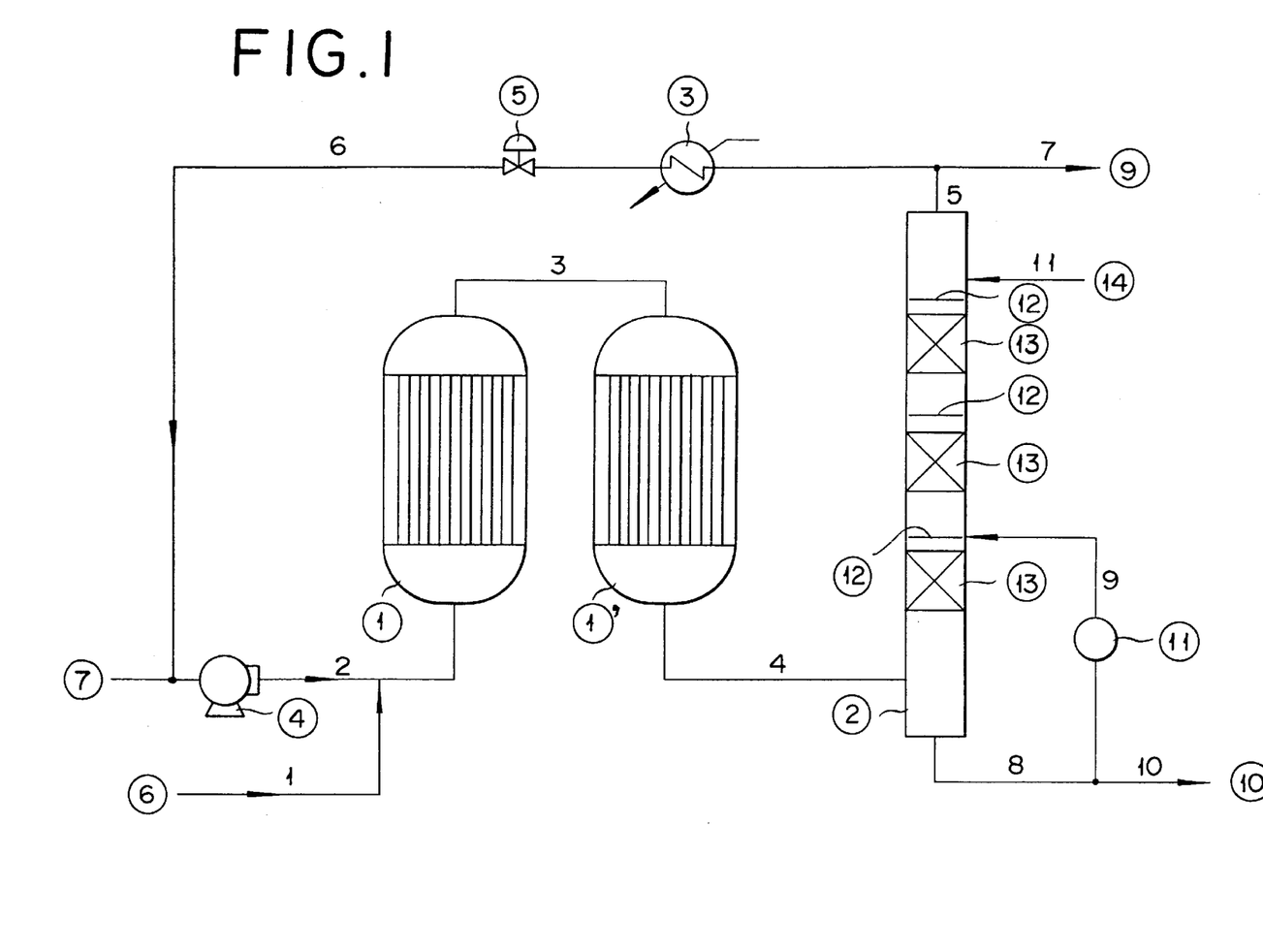
FIG. 1 is a diagram illustrating a process for the production of (meth)acrylic acid, furnished in an effluent gas pipe extended from a absorption column to a step of reaction with a heat-exchanger as one preferred embodiment of this invention.

The step for the absorption mentioned above comprises such actions as introducing a (meth)acrylic acid-containing gas through a line 4 into a absorption column ② and meanwhile introducing a absorbent ⑭ for absorbing (meth)acrylic acid from above the absorption column via a line 11 into the column, and advancing the absorbent into counterflow contact with the gas mentioned above thereby inducing the absorption of (meth)acrylic acid by the absorbent. The absorption column to be effectively used herein may be any of the known absorbing columns such as plate columns, packed columns, wetted-wall columns, and spray columns, for example. Generally, plate columns or packed columns prove particularly advantageous among other absorption columns. They use plates or packing materials as their contents. The packed column is filled regularly or irregularly with packing materials which have a large surface area and exhibit perviousness to gas. The surface of a packed bed which is filled with the packing materials forms the site for gas-liquid contact.

As concrete examples of the solvent to be supplied, such known solvents such as water, organic acid-containing water, and high boiling inactive hydrophilic organic liquids (diphenylether, diphenyl, etc.) may be cited. These solvents may be used either singly or in the form of a mixture of two or more members. It is commendable for these solvents to incorporate properly therein such known polymerization inhibitors such as methoquinone, manganese acetate, nitrosophenol, cupferron, N-oxyl compounds, copper dibutyl thiocarbamate, phenothiazine, and hydroquinone for the purpose of preventing such polymerizing substances as (meth)acrylic acid from succumbing to polymerization.

The operating conditions of the absorption column are decided by such factors as the pressure, temperature, composition of liquid absorbent, and amount of the absorbent. Under the conditions which prove advantageous, the temperature is low and the amount of the liquid absorbent is large. Since these conditions are prone to constraints of the subsequent step, proper conditions are set by taking into due respect such factors as mentioned above. Further, since it has been confirmed that the ease with which the (meth)acrylic acid succumbs to polymerization is varied by the concentration of this acid in the liquid phase in the absorption column, it is commendable to change the kind of filling material based on the concentration of the (meth)acrylic acid. Generally, when the (meth)acrylic acid concentration in the liquid phase in the column interior is in the range of 3–60 weight %, preferably 4–40 weight %, and more preferably 5–30 weight % in the steady state of absorption, it is proper for the solution adhering to the plates or the packed bed ⑬ and the distributer ⑫ to be divided into the part of the solution falling on the inner charge side having a lower concentration than the concentration mentioned above as an upstream and the part of the solution falling on the inner charge side having a higher concentration than the concentration mentioned above as a downstream. By having the packed beds filled with packing materials or the plates disposed generally in a plurality of numbers on the upstream and on the downstream as divided in the manner described above, it is made possible to attain efficient absorption of the (meth)acrylic acid in the solvent and meanwhile repress otherwise possible polymerization of the (meth)acrylic acid.

Subsequently, this invention proceeds to circulate part or the whole of the discharged gas occurring at the step of absorption via an effluent gas pipe connecting the step for absorption to the step for reaction. This circulation may be effected directly on the discharged gas emanating from the step of absorption or indirectly on the discharged gas after it gas has been converted into an inactive gas by the combustion of the organic substance contained therein. The effluent gas pipe used herein does not need to be particularly discriminated on account of the material to be used therefore. It may be properly laid with the same steel material as that of the pipe to be used for supplying the acrylic acid-containing solution. As concrete examples of the effluent gas pipe, austenite type steel pipes, austenite ferrite type steel pipes, and ferrite type steel pipes, and carbon steel pipes may be cited.

This invention pertains, in the operation for the production of acrylic acid which at least comprises the process mentioned above and the piping also mentioned above, to a method for preventing the effluent gas pipe from blocking. This method will be described below with reference to FIG. 1 which depicts an example of the operation which proceeds through the step of the reaction of contact gas phase oxidation of acrylic acid.

For a start, the raw material ⑥ such as propylene is supplied via a line 1 and an inert gas ⑦ is supplied via a line 2, both to a reactor ①. The reactor ① which is packed in advance with an oxidizing catalyst, consequently forms a mixed gas containing acrolein. This gas is supplied via a line 3 to a reactor ①' to induce formation of acrylic acid from acrolein. The gas component consequently obtained contains substances such as adlehyde which have lower boiling points than (meth)acrylic acid, carboxylic acids such as terephthalic acid and benzoic acid which have higher boiling points than the (meth)acrylic acid, and by-products such as tarry substances which have comparatively high boiling points besides the acrylic acid as the target product. The acrylic acid-containing gas mentioned above, therefore, is supplied to an acrylic acid absorption column ② to induce absorption of the acrylic acid in the absorbent. The term "low boiling substances" as used herein refers to substances having lower boiling points than the (meth)acrylic acid and the term "high boiling substance" as used herein refers to substances having higher boiling points than the (meth) acrylic acid.

In the absorption column ②, such absorbents as a solvent sparingly soluble in water containing acrylic acid and acetic acid, a aqueous solution containing acrylic acid and acetic acid, a solvent sparingly soluble in water, or water itself is advanced into counterflow contact with the acrylic acid to effect absorption thereof. The acrylic acid thus absorbed, depending on the composition of the absorbent to be used, is either recovered through the medium of a cooler ⑪ disposed in the absorption column and supplied as a solution containing acrylic acid in a high concentration from the bottom of the column via lines 8 and 10 to a step for purification ⑩ (not shown). Properly in this invention, the temperature of the gas discharged through the top of the absorption column ② is adjusted in the range of 30–70° C., preferably 40–65° C., and particularly preferably 40–60° C., without reference to the kind of the absorbent in use. Incidentally, the temperature of the discharged gas is variable with the concentrations of the raw material gases supplied to the reactors ① and ①', the temperature of the reaction gas supplied to the absorption column, and the temperature of the absorbent. The term "temperature of the discharged gas" as used in this invention, therefore, means the average temperature per unit time.

The temperature of the discharged gas is adjusted as being properly varied with the temperature of the absorbent, the amount of the liquid circulated through the cooler per unit time, and the cooling capacity of the cooler connected to the absorption column, for example. It has been ascertained that by setting the temperature of the top of the column, among other operating conditions of the known absorption column, in the aforementioned range, it is made possible not only to attain sufficient absorption of the (meth)acrylic acid gas in the absorbent but also to effect absorption of formaldehyde as a low boiling substance and terephthalic acid as a subliming substance, for example, in the absorbent and restrain the otherwise possible migration of such extraneous substances into the discharged gas. It is consequently made possible to adjust the amounts of the (meth)acrylic acid, low boiling substance, and subliming substance to be discarded into the discharged gas, prevent effectively the interior of the effluent gas pipe from being blocked in consequence of the deposition of such extraneous substances, prevent the other steps for the production of (meth)acrylic acid subsequent to the absorption column from being likewise blocked, and permit effective reclamation of the discharged gas. If the temperature falls short of 30° C., the shortage will necessitate use of a proper amount of a heat exchange grade refrigerant for cooling the gas component in the absorption column, induce an undue rise of the concentration of blocking substances in the column bottom liquid, and entail the problem of blockage at the subsequent steps for the production of (meth)acrylic acid. If the temperature conversely exceeds 70° C., the excess will not merely lower the ratio of absorption of the (meth)acrylic acid in the absorbent but also add to the concentration of the subliming substance in the gas discharged from the absorption column, with the result that the cyclic use of the discharged gas at the step for reaction will be rendered difficult. Further, the step for purification ⑩ subsequent to the production of (meth) acrylic acid to which the column bottom liquid is supplied via the lines 8 and 10 can be prevented from succumbing to such hindrances as polymerization and blockage by causing the discharged gas to be discarded at the temperature of the top of the absorption column mentioned above and the amount of the inert gas to be discarded can be decreased by effectively recirculating the discharged gas. Thus, these measures both contribute to the conservation of the environment and excel in economy as well.

Properly, the temperature of the discharged gas at the top of the absorption column ② mentioned above is adjusted particularly by drawing the column bottom liquid through the line 8, transferring it to the cooler ⑪, cooling it therein, and then changing the cooling power of the cooler ⑪ furnished for the purpose of circulating the liquid via the line 9 to the interior of the column. This particular procedure is preferable because of the convenience of the operation. If the amount of the absorbent relative to the amount of the reacting gas supplied to the absorption column ② and the temperature of the absorbent are changed, such changes will vary the concentration of the (meth)acrylic acid in the column bottom liquid possibly to the extent of degrading the separating capacity at the subsequent step. For the purpose of adjusting the temperature of the top of the absorption column ② by cooling the column top with the cooler ⑪ in the manner described above, the amount of the gas discharged from the reactor for catalytic gas phase oxidation and supplied to the absorption column is generally in the range of 2–15 liters/m$^3$ of the absorbent, preferably 3–12 liters m$^3$, and particularly preferably 5–10 liters m$^3$. Incidentally, the waste gas emanating from the absorption column has a composition consisting of 0.001–0.5 vol. % of terephthalic acid and formaldehyde, 3–50 vol. % of water, and 0.01–0.2 vol. % of other organic substances (the balance of an inert gas).

This invention contemplates circulating the gas discharged through the top of the absorption column ② through the effluent gas pipe indicated as lines 5 and 6 to the step of reaction. The circulation does not need to be limited to the whole amount of the discharged gas. It may be effected, when necessary, on part of the discharged gas, with the remainder allowed to be discarded as a waste gas ⑨ through the step of combustion via the line 7 which is branched from the line 5. Even in the effluent gas pipe which is connected to the site for disposal of the discharged gas, however, the blockage of the interior of this pipe can be efficiently prevented by using the temperature elevation and the application of pressure in the interior of the effluent gas pipe. For this purpose, the method of this invention for preventing the blockage can be adopted.

In the effluent gas pipe which either circulates the discharged gas to the step for reaction or serves as a flow path for the discharged gas to the cite for disposal by discarding, the temperature of the discharged gas derived from the absorption column ② is either kept intact at the original temperature or elevated to 0–50° C., preferably 5–40° C., and particularly preferably 10–30° C. above the original temperature. The discharged gas contains the inert gas and such low boiling substances as formaldehyde by-produced at the step of reaction and such subliming substances as terephthalic acid invariably in a gaseous state. By securing the temperature mentioned above, it is made possible to control the temperature of the gas flowing the interior of the effluent gas pipe constantly in the range of 30–120° C., maintain the discharged gas in the gaseous state and attain effective prevention of the formation of a polycondensate in the effluent gas pipe and the fast adhesion of a sublimate on the inner wall of the pipe, and consequently preclude the otherwise possible blockage of the pipe with the solidified polycondensate or the deposited sublimate. If the water contained in the discharged gas is suffered to condense and adhere to the blades of the air blower disposed inside the pipe, the condensate will degrade the capacity of the blower and induce corrosion of the blower. By elevating the temperature to the level specified above, these hindrances can be effectively prevented. The elevation of the temperature to below 0° C. means that the gas is cooled and, therefore, this decline of the temperature will pose the phenomena of condensation and adhesion as problems. Conversely, if the temperature so elevated surpasses 50° C., the excess will prove uneconomical on account of not only necessitating an unduly large heat source but also resulting in enlarging the air blower. In the range of the composition of the components contained in the discharged gas derived from the step for the reaction of the (meth)acrylic acid and the step for the absorption thereof, the components contained in the range mentioned above can be maintained in the gaseous state, with the characteristic properties of the components as a contributory factor. Particularly, the terephthalic acid, for example, can be maintained thoroughly in the gaseous state in the range of temperature mentioned above because it is a subliming compound, while it is a high boiling substance as well. Since the temperature of the discharged gas is defined in the specification hereof as the average temperature per unit time, the expression "the temperature, 30–120° C., of the discharged gas flowing the interior of the effluent gas pipe" is construed as meaning the average temperature per unit time.

Incidentally, the expression "the temperature elevation to 0° C." reflects the case in which the actual temperature of the gas is not changed even by the temperature elevation because the discharged gas in the effluent gas pipe is cooled by the cold air outside the effluent gas pipe. Where the discharged gas can be circulated to the reactor for catalytic oxidation with the temperature thereof kept intact, this discharged gas is not cooled and consequently is not suffered to induce such phenomena as condensation, adhesion, and blockage inside the effluent gas pipe. The case in which the temperature of the discharged gas can be kept intact at the original temperature without requiring any operation for temperature elevation because of the provision of a heat insulating mechanism of one sort or other, therefore, is embraced in this invention.

Figure 2:
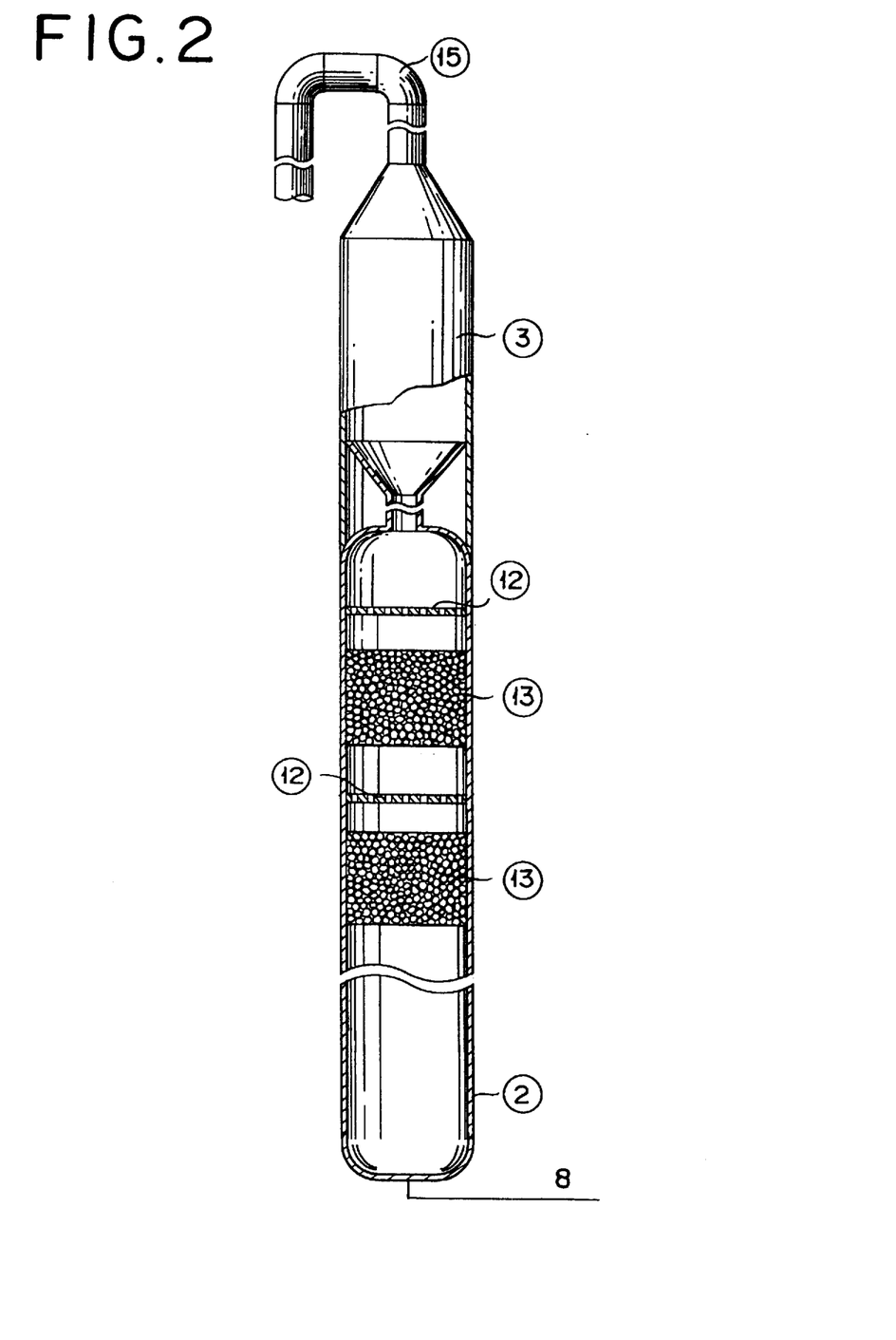
FIG. 2 is a diagram illustrating the manner of disposition of the heat exchanger relative to the absorbing column.

For the purpose of attaining the temperature elevation of the nature described above, it is proper to connect the top part of the absorption column ② directly to the heat exchanger ③ without intervention of an effluent gas pipe ⑮ and dispose the effluent gas pipe ⑮ in the outlet part of the heat exchanger ③ as illustrated in FIG. 2. The so-called finned tube type or plate type can be used for this heat exchanger. The use of this type is commendable because this type excels in the ratio of heat exchange as evinced by the fact that the heating surface area thereof is three times as high as that the shell-and-tube type heat exchanger. The type is further capable of rapid heating. In contrast, the method which relies on the use of an effluent gas pipe coated with a jacket necessitates a pipe of huge length for the purpose of securing a necessary heating surface area, encounters difficulty in attaining temperature elevation in a short period of time because of the small heating surface area per unit volume, and consequently possibly induces formation of a deposit on the inner wall of the pipe. The device for the temperature elevation of this nature is provided for the purpose of elevating the temperature of the discharged gas and allowing the discharged gas to maintain the gaseous state and, therefore, is properly disposed in direct contact with the effluent gas outlet of the absorption column ② as illustrated in FIG. 2 or disposed in the proximity thereof. When this disposition is not practicable on account of the problem of piping, however, the device is disposed in the closest proximity to the discharge outlet mentioned above to secure the elevation of the gas temperature. For the sake of maintaining the gas component inside the pipe in the gaseous state, it is permissible to provide the pipe with a plurality of heat exchangers. It is further permissible to lay the gas lines 6 and 7 separately of each other.

In this invention, the discharged gas is preferred to be compressed in these line or these pipes. By using this compression for adjusting the linear velocity of the discharged gas in the effluent gas pipe, it is made possible to prevent the otherwise possible deposition of a condensate on the inner wall of the effluent gas pipe. Properly, a compressor or an air blower may be installed as a means to implement this compression. The term "compression" as used in the specification hereof means that the pressure of the discharged gas discarded from the absorption column ② is further exalted. Since the pressure is variable with the temperature, the discharged gas is compressed simultaneously with the temperature elevation when this temperature elevation is accompanied by an increases in the pressure. There are times when the discharged gas is compressed even in the absence of an operation for artificial compression.

Properly, the linear velocity of the discharged gas is in the range of 5–40 m/s, preferably 10–30 m/s, and particularly preferably 15–25 m/s. If the linear velocity falls short of 5 m/s, the shortage will induce the gas component to stagnate and consequently entail adhesion of the gas component itself or of the condensate derived therefrom to the inner wall of the effluent gas pipe possibly to the extent of blocking the pipe. Conversely, if the linear velocity exceeds 40 m/s, the excess will bring about aggravation of the pressure loss and induce the adhesion mentioned above to the bent parts of the pipe, with the result that the pipe will be eventually corroded. This necessary linear velocity can be attained by connecting a compressor such as, for example, an air blower ④ capable of compressing the discharged gas to the effluent gas pipe or by adjusting the diameter of the pipe. By setting the linear velocity at a level in the range specified above, the mist contained in the reaction gas of the (meth) acrylic acid can be prevented from inducing adhesion of water to the blades of the air blower, consequently degrading the working capacity of the blower, and corroding the air blower.

Incidentally, the linear velocity of the discharged gas varies because it is changed by such factors as the flow volume of the raw material gas supplied to the reactors ① and ①', the temperature of the effluent gas pipe line 4, and the pressure of the absorption column ② as mentioned above. In this invention, therefore, the expression "linear velocity of the discharged gas" is construed to mean the average linear velocity at a specific position in the effluent gas pipe per unit time. The sentence "the linear velocity is in the range of 5–40 m/s," therefore, does not necessarily mean the average linear velocity throughout the entire length of the effluent gas pipe but means the requirement "5–40 m/s" satisfied at any point in the effluent gas pipe.

In this invention, the effluent gas pipe is connected to the line for supply of the inert gas, i.e. the line 6 illustrated in FIG. 1. By installing a flow volume adjusting device ⑤ halfway in the length of the line extending from the effluent gas pipe to the reactor, the discharged gas containing the inert gas in a large amount can be stably supplied and used in the reaction for catalytic gas phase oxidation.

This invention permits production of acrylic acid by causing the acrylic acid-containing solution emanating from the bottom of the absorption column ② to the step for purification (not shown) which continues from the absorption column ②. This step for purification may embrace any of the known steps which are capable of purification.

The invention has been described above with respect to an example of the production of acrylic acid. It may be embodied in the production of methacrylic acid by changing properly the raw materials to be supplied to the reactors ① and ①'.

This invention, when the gas discharged at the step for absorption is circulated for reuse or discarded through the medium of the effluent gas pipe, prefers the mist contained in the discharged gas to be separated for removal. When the mist is suffered to float in the interior of the effluent gas pipe, the discharged gas being recycled therethrough induces adhesion of scale to the pipes and the devices which are destined to pass the discharged gas. When the degree with which this adhesion occurs is great, the operator of the apparatus will be possibly obliged to discontinue the operation of the apparatus and remove the scale artificially or chemically. The adhesion of the scale which is caused by the discharged gas emanating from the absorption column, however, can be effectively prevented by stripping the gas of the mist. By removing the mist in advance, therefore, the blockage of the interior of the effluent gas pipe possibly involved during the cyclic use or the disposal by discarding of the discharged gas through the medium of the effluent gas pipe can be prevented even when the treatment for adjusting the temperature of the discharged gas to the temperature of the discharged gas emanating from the step for absorption or maintaining this temperature at the same temperature is omitted. When the temperature of the discharged gas from the absorption column is adjusted to the same temperature as that of the discharged gas emanating from the step for absorption, the removal of the mist may be implemented before and/or after the temperature elevation of the discharged gas. Especially, the removal of the mist treatment while the temperature of the discharged gas is maintaining in the gas pipe can prevent the pipe from blocking effectively in comparison with just the maintaining of the temperature treatment. The term "mist" as used in the specification hereof is construed to refer generally to all the liquid and solid substances floating in the gas.

The separation for removal of the mist from the discharged gas can be implemented by using a mist separator which is popularly used for the separation for removal of mist. Among other types of mist separator, the gravity separation type mist separator, centrifugal separation type mist separator, and collision separation type mist separator are advantageously used.

As regards the size of the particles of mist to be separated for removal, the separation is commended to remove the particles of mist to the smallest possible size. The separation for removal of the mist particles measuring approximately 1000 μm, preferably approximately 800 μm, in minimum diameter permits effective prevention of the adhesion of blocking substances. Particularly by separating for removal of the particles of mist measuring approximately 100 μm, or approximately 40 μm, or even approximately 10 μm, in diameter, it is made possible to permit more effective prevention of the adhesion of blocking substances. Incidentally, an effort to separate for removal the mist particles measuring not more than 10 μm in diameter possibly result in inducing adhesion of such fine mist particles to the mist separator itself.

In this invention, therefore, it is commendable to implement the separation for removal of the mist by the use of the gravity separation type, centrifugal separation type, or collision separation type mist separator whose minimum mist diameter for absorption (the smallest diameter of the mist particles capable of theoretical absorption to 100%) is approximately 100 μm, or approximately 40 μm, or even approximately 10 μm, in diameter. In the case of the collision separation type mist separator, it is commendable for this mist separator to have as simple a construction as permissible in due consideration of the possibility of the mist separator itself being clogged with adhering matter.

The mist separator mentioned above does not need to be particularly discriminated on account of the place to be selected for installation. It may be installed in the pipe laid immediately after the absorption column, the pipe for recycling the discharged gas as a diluting gas to the reactor for gas phase oxidation (such as, for example, in front of the blower or the heat exchanger disposed in the pipe), or the pipe for leading the discharged gas such as to a combustion device for the sake of disposal by combustion. One mist separator may be used or a plurality of mist separators installed separately at as many positions may be used.

The third aspect of this invention relates, in the process for the production of (meth)acrylic acid which comprises at least a step for the reaction of catalytic gas phase oxidation of (meth)acrylic acid and a step for the absorption of the product of the reaction, to a method for the production of (meth)acrylic acid, characterized by causing part or the whole of discharged gas having a gas outlet temperature in the range of 30–70° C. at the step for absorption, while being circulated through an effluent gas pipe to the step for reaction, to be either maintained at the same temperature as the temperature of the discharged gas from the step for absorption or elevated to a higher temperature and to be compressed at the same time. By setting the gas outlet temperature at a level in the range of 30–70° C. at the step for absorption as described above, it is made possible to adjust the amounts of such low boiling substances as formaldehyde and such subliming substances as terephthalic acid which are contained in the discharged gas in a preferred range. By adjusting the temperature in the range specified above, therefore, the relevant components can be effectively reused directly in the step for reaction. If the amounts of low boiling substances and subliming substances to be contained in the (meth)acrylic acid-containing solution emanating from the absorption column are large, these extraneous substances will induce such adverse phenomena as adhesion of and blockage with a polycondensate at the subsequent step for purification. This invention precludes these phenomena and consequently prevents the blockage at the step for the production of (meth)acrylic acid.

In the third aspect of this invention, the elevated temperature of the pipe mentioned above is in the same range of 0–50° C. as explained and defined in the first aspect of the invention. The more preferred range of this temperature and the reason therefor are the same as described in the first aspect of this invention. The linear velocity of the discharged gas is preferred to be in the same range as described and defined in the first aspect of this invention and the reason therefore is the same as in the first aspect of the invention. The blockage occurring in the effluent gas pipe and the degradation of the capacity of the air blower obstruct the reclamation of the discharged gas from the absorption column. The discharged gas can be efficiently utilized, however, by precluding the blockage.

The mode of "maintaining the temperature of the discharged gas at the same temperature as that of the discharged gas from the step for absorption or elevating this temperature to a higher level" contemplated in the third aspect of this invention can embrace any of the modes of embodying the method for "preventing the effluent gas pipe from blocking" recited in the first and the second aspect of this invention.

EXAMPLES

Now, this invention will be described more specifically below with reference to working examples.

Example 1

The reaction and the absorption of acrylic acid were carried out by the use of an apparatus for the production of acrylic acid illustrated in FIG. 1. A raw material gas composed of 7 vol. % of propylene, 12 vol. % of oxygen, 7 vol. % of water, and 74 vol. % of other inert gas was supplied at a rate of 410 Nm³ per hour to a reactor ①.

The reaction gas derived from a reactor ①' had a temperature of 280° C. and was composed of 5.8 vol % of acrylic acid, 14.8 vol. % of water, 76.3 vol. % of the inert gas, and a total of 3.1 vol. % of acetic acid, terephthalic acid, formaldehyde, maleic acid, etc. The acrylic acid-containing gas was cooled to 150° C. and then supplied to a absorption column ②. The absorption column ② was filled from the lower part thereof upward with one packed bed of Cascade Miniring 2P (made by Dodwell Corp) 400 mm in inside diameter and 2000 mm in length, two packed beds of Cascade Miniring 2P 250 mm in inside diameter and 2150 mm in length, and two packed beds of SULZER BX (made by Sumitomo Heavy Industries, Co. LTD.) 250 mm in inside diameter and 1580 mm in length. Here, the water containing 100 weight ppm of hydroquinone as a polymerization inhibitor was used as an absorbent. This absorbent adjusted in advance to 40° C. was supplied at a rate of 50 liters/hour to the absorption column ②. Then, the column bottom liquid was circulated via the cooler ⑪ to the absorption column ② so that the column top temperature was cooled to 60° C.

The absorption column was operated to absorb the acrylic acid, with the column top pressure adjusted to 10000 Pa as a gauge pressure. The gas discharged through the column top had a temperature of 60° C. and was composed of 0.04 vol. % of acrylic acid, 17.9 vol. % of water, 81.77 vol. % of the inert gas, a total of 0.29 vol. % of other low boiling substances, and a total of 0.05 vol ppm of subliming substances.

Then, part of the discharged gas consequently obtained was supplied at a flow volume of 146 Nm$^3$ per hour to a finned-tube type heat exchanger and heated therein up to 85° C. and circulated through a line 6 to the reactor ①. The discharged gas was used with the amount of supply thereof to the reactor ① adjusted in advance through the medium of a flow volume adjuster ⑤ provided in the line 6. The gas in the interior of the effluent gas pipe had a temperature of 84.7° C. The minimum part of the linear velocity including the heat exchanger was 6m/s and the maximum part thereof was 38 m/s. The temperatures and the linear velocities reported in Example 1 were average values per unit time.

When the circulation gas line was inspected after one month's continued operation of the apparatus, no adhering deposit was detected. When the compressor was inspected after one year's continued operation of the apparatus, absolutely no sign of corrosion or blockage was detected.

The column bottom liquid obtained in the absorption column ② was supplied through lines 8 and 10 to a purification column not shown in the diagram. The column bottom liquid was found to have an acrylic acid concentration of 62.4 weight %. When the interior of the purification column was inspected after one year's continued operation of the apparatus, absolutely no sign of corrosion or blockage was detected.

Comparative Example 1

The apparatus was operated under the same conditions as in Example 1 excepting the omission of the temperature elevation of the waste gas. The gas in the interior of the effluent gas pipe had a temperature of 59.8° C.

When the circulation gas line was inspected after one month's continued operation of the apparatus, deposition of adhering matter was observed throughout the entire inner wall of the line and adhesion of polycondensates of terephthalic acid and formaldehyde in large amounts was observed particularly on the valve for controlling the flow volume of the circulation gas. When the compressor was inspected after one year's continued operation of the apparatus, the impeller part was found to have suspended wear possibly ascribable to the mist.

The column bottom liquid obtained in the absorption column ② was supplied through the lines 8 and 10 to the purification column not shown in the diagram. Incidentally, the column bottom liquid was found to have an acrylic acid concentration of 62.4 weight %. When the interior of the purification column was inspected after one year's continued operation of the apparatus, absolutely no sign of corrosion or blockage was detected.

Example 2

The apparatus for the production of acrylic acid illustrated in FIG. 1 was used and operated in the same manner as in Example 1 to obtain a discharged gas from the absorption column ②. Then, the discharged gas was circulated to the reactor ① by following the procedure of Example 1 while changing the elevated temperature of the discharged gas to 110° C. The gas in the interior of the effluent gas pipe had a temperature of 109.5° C. The minimum part of the linear velocity including the heat exchanger was 3 m/s and the maximum part thereof was 41 m/s. The temperatures and the linear velocities reported in Example 2 were average values per unit time.

When the circulation gas line was inspected after one month's continued operation of the apparatus, deposition of adhering matter was observed, though slightly, in the parts having a linear velocity of less than 5 m/s and a linear velocity of more than 40 m/s. When the compressor was inspected after one year's continued operation of the apparatus, no conspicuous sign of blockage or corrosion was detected.

The column bottom liquid obtained in the absorption column ② was supplied through the lines 8 and 10 to the purification column not shown in the diagram. Incidentally, the column bottom liquid had the same composition as in Example 1. When the interior of the purification column was inspected after one year's continued operation of the apparatus, absolute no sign of corrosion or blockage was detected.

Example 3

The apparatus for the production of acrylic acid illustrated in FIG. 1 was used and operated for the reaction and the absorption of acrylic acid. The raw material gas composed of 7 vol. % of propylene, 13 vol. % of oxygen, 7 vol. % of water, and 73 vol. % of other inert gas was supplied at a rate of 399 Nm$^3$ per hour to the reactor ①.

The reaction gas derived from the reactor ①' had a temperature of 280° C. and was composed of 6.0 vol. % of acrylic acid, 15.4 vol. % of water, 75.5 vol. % of the inert gas, and a total of 3.1 vol. % of terephthalic acid, formaldehyde, and maleic acid. The acrylic acid-containing gas was supplied at a temperature of 150° C. to the absorption column ②. The absorption column ② was filled from the lower part thereof upward with a packed bed of Cascade Miniring 2P (made by Dodwell Corp) 400 mm in inside diameter and 2000 mm in length, two packed beds of Cascade Miniring 2P 250 mm in inside diameter and 2150 mm in length, and two packed beds of SULZER BX (made by Sumitomo Heavy Industries, Co. LTD.) 250 mm in inside diameter and 1580 mm in length. Here, the water containing 100 weight ppm of hydroquinone as a polymerization inhibitor was used as an absorbent. This absorbent was supplied at a rate of 25 liters/hour to the absorption column ②, with the temperature thereof adjusted in advance to 40° C. At the same time, the column button liquid was circulated via the cooler ⑪ to the absorption column ②, with the tower top temperature cooled in advance to 43° C.

The absorption column was operated under a working pressure of 10000 Pa as a gauge pressure to absorb the formed acrylic acid. The gas discharged through the column top had a temperature of 43° C. and was composed of 0.001 vol. % of acrylic acid, 7.8 vol. % of water, 91.90 vol. % of the inert gas, a total of 0.3 vol. % of low boiling substances, and a total of 0.03 vol ppm of subliming substances.

Then, part of the discharged gas consequently obtained was supplied at a rate of 118 Nm³ per hour to a finned-tube type heat exchanger, heated therein up to 90° C., and circulated through the line 6 to the reactor ①. The discharged gas was used, with the amount thereof supplied to the reactor ① adjusted in advance through the medium of the flow volume adjuster ⑤ disposed in the line 6. The gas in the interior of the effluent gas pipe had a temperature of 89.7° C. The minimum part of the linear velocity including the heat exchanger was 5 m/s and the maximum part thereof was 32 m/s. The temperatures and the linear velocities reported in Example 3 were average values per unit time.

When the circulation gas line was inspected after one month's continued operation of the apparatus, no sign of deposition of adhering matter was detected. When the compressor was inspected after one year's continued operation of the apparatus, absolutely no sign of corrosion or blockage was detected.

The column bottom liquid obtained in the absorption column ② was supplied through the lines 8 and 10 to the purification column not shown in the diagram. Incidentally, the column bottom liquid had an acrylic acid concentration of 57.6 weight %. When the interior of the purification column was inspected after one year's continued operation of the apparatus, absolutely no sign of corrosion or blockage was detected.

Example 4

The apparatus for the production of acrylic acid illustrated in FIG. 1 was used and operated for the reaction and the absorption of acrylic acid. The raw material gas composed of 7 vol. % of propylene, 12 vol. % of oxygen, 6 vol. % of water, and 75 vol. % of the inert gas was supplied at a rate of 399 Nm³ per hour to the reactor ①.

The reaction gas obtained from the reactor ①' had a temperature of 280° C. and was composed of 6.0 vol. % of acrylic acid, 13.9 vol. % of water, 77.0 vol. % of the inert gas, and a total of 3.1 vol. % of terephthalic acid, formaldehyde, and maleic acid. The acrylic acid-containing gas was supplied at a temperature of 150° C. to the absorption column ②. The absorption column ② was filled from the lower part thereof upward with a packed bed of Cascade Miniring 2P (made by Dodwell Corp) 400 mm in inside diameter and 2000 mm in length, two packed beds of Cascade Miniring 2P 250 mm in inside diameter and 2150 mm in length, and two packed beds of SULZER BX (made by Sumitomo Heavy Industries, Co. LTD.) 250 mm in inside diameter and 1580 mm in length. Here, the water containing 100 weight ppm of hydroquinone as a polymerization inhibitor was used as an absorbent. This absorbent was supplied at a rate of 25 liters/hour to the absorption column ②, with the temperature thereof adjusted in advance to 40° C. At the same time, the column button liquid was circulated via the cooler ⑪ to the absorption column ②, with the tower top temperature cooled in advance to 25° C.

The absorption column was operated under a working pressure of 10000 Pa as a gauge pressure to absorb the acrylic acid. The gas discharged through the column top had a temperature of 25° C. and was composed of 2.8 vol. % of water, 97.00 vol. % of the inert gas, a total of 0.2 vol. % of low boiling substances, and a total of 0.01 vol ppm of subliming substances. No acrylic acid was detected in the gas.

Then, part of the waste gas consequently obtained was supplied at a rate of 118 Nm³ per hour to a finned-tube type heat exchanger, heated therein up to 90° C., and circulated through the line 6 to the reactor ①. The discharged gas was used, with the amount thereof supplied to the reactor ① adjusted in advance through the medium of the flow volume adjuster ⑤ disposed in the line 6. The gas in the interior of the effluent gas pipe had a temperature of 89.7° C. The minimum part of the linear velocity including the heat exchanger was 5 m/s and the maximum part thereof was 32 m/s. The temperatures and the linear velocities reported in Example 4 were average values per unit time.

When the circulation gas line was inspected after one month's continued operation of the apparatus, no sign of deposition of adhering matter was detected. When the compressor was inspected after one year's continued operation of the apparatus, absolutely no sign of corrosion or blockage was detected in particular.

The column bottom liquid obtained in the absorption column ②was supplied through the lines 8 and 10 to the purification column not shown in the diagram. Incidentally, the column bottom liquid had an acrylic acid concentration of 54.0 weight %. When the interior of the purification column was inspected after one year's continued operation of the apparatus, adherence of a polymer was detected in the line interconnecting the column top and the condenser and in the line interconnecting the condenser and a vacuum generating device.

Example 5

The apparatus for the production of acrylic acid illustrated in FIG. 1 was used and operated for the reaction and the absorption of acrylic acid. The raw material gas composed of 7 vol. % of propylene, 12 vol. % of oxygen, 8 vol. % of water, and 73 vol. % of the inert gas was supplied at a rate of 410 Nm³ per hour to the reactor ①.

The reaction gas obtained from the reactor ①' had a temperature of 280° C. and was composed of 5.8 vol. % of acrylic acid, 15.6 vol. % of water, 75.5 vol. % of the inert gas, and a total of 3.1 vol. % of terephthalic acid, formaldehyde, and maleic acid. The acrylic acid-containing gas was supplied at a temperature of 180° C. to the absorption column ②. The absorption column ② was filled from the lower part thereof upward with a packed bed of Cascade Miniring 2P (made by Dodwell Corp) 400 mm in inside diameter and 2000 mm in length, two packed beds of Cascade Miniring 2P 250 mm in inside diameter and 2150 mm in length, and two packed beds of SULZER BX (made by Sumitomo Heavy Industries, Co. LTD.) 250 mm in inside diameter and 1580 mm in length. Here, the water containing 100 weight ppm of hydroquinone as a polymerization inhibitor was used as an absorbent. This absorbent was supplied at a rate of 90 liters/hour to the absorption column ②, with the temperature thereof adjusted in advance to 60° C. At the same time, the column bottom liquid was circulated via the cooler ⑪ to the absorption column ②, with the tower top temperature cooled in advance to 70° C.

The absorption column was operated under a working pressure of 10000 Pa (gauge pressure) to absorb the acrylic acid. The gas discharged through the column top had a temperature of 70° C. and was composed of 0.02 vol. % of acrylic acid, 28.3 vol. % of water, 71.48 vol. % of the inert gas, a total of 0.02 vol. % of low boiling substances, and a total of 0.04 vol ppm of subliming substances.

Then, the discharged gas consequently obtained was burned in its whole amount part to obtain an inert gas. Part of the inert gas was supplied at a rate of 140 Nm³ per hour to a finned-tube type heat exchanger, heated therein up to 80° C., and circulated through the line 6 to the reactor ①. The discharged gas was used, with the amount thereof supplied to the reactor ① adjusted in advance through the medium of the flow volume adjuster ⑤ disposed in the line 6. The gas in the interior of the effluent gas pipe had a temperature of 79.9° C. The minimum part of the linear velocity was 18 m/s and the maximum part thereof was 20 m/s. The tempeatures and the linear velocities reported in Example 5 were average values per unit time.

When the circulation gas line was inspected after one month's continued operation of the apparatus, no sign of deposition of adhering matter was detected. When the compressor was inspected after one year 's continued operation of the apparatus, absolutely no sign of corrosion or blockage was detected in particular.

The column bottom liquid obtained in the absorption column ② was supplied through the lines 8 and 10 to the purification column not shown in the diagram. Incidentally, the column bottom liquid had an acrylic acid concentration of 64.0 weight %. When the interior of the purification column was inspected after one year's continued operation of the apparatus, absolutely no sign of corrosion or blockage was detected.

Example 6

A collision separation type mist separator capable of absorbing mist particles of a minimum diameter of 40 $\mu$m was installed in a pipe interconnecting the absorption column and a waste gas combustion device and used to test for the deposition of scale as described below.

The acrylic acid-containing gas obtained by subjecting propylene to gas phase oxidation in the presence of an oxidizing catalyst was introduced under the following condition to effect absorption of liquid. Then, the discharged gas emanating from the top part of the absorption column was wholly transferred through the mist separator to the combustion device.

During a six-month continued operation of the apparatus, no sign of rise was detected in the pressure loss. When the pipes and the devices installed downstream of the mist separator were opened and inspected after six months' continued operation, substantially no sign of adhesion of scale was detected.

<Operating Conditions>

Reaction gas:

Amount introduced; 400 Nm³/h
Composition; 5.8 vol. % of acrylic acid, 15.5 vol. %
of water, 73.6 vol. % of nitrogen, 2 vol. % of oxygen,
and others (such as acetic acid)
Column top pressure; 10 kPa (Gauge)
Column top temperature; 62.5° C.
Absorbent:

Liquid; Water (containing 100 weight ppm of hydroquinone
as polymerization inhibior)
Amount suppliied; 50 liters/h Example 7

The test for scale adhesion was performed by following the procedure of Example 6 while using a gravity separation type mist separator capable of absorbing mist particles of a minimum diameter of 800 $\mu$m instead as a mist separator.

The apparatus could be operated for six months continuously, though a rise of roughly some tens of Pa was detected in the pressure loss. When the pipes and the devices installed downstream of the mist separator were opened and inspected after six months' operation of the apparatus, adhesion of scale was partly detected.

Comparative Example 2

The test for scale adhesion was carried out by following the procedure of Example 6 while the provision of the mist separator was omitted.

A sign of rise in the pressure loss appeared after the start of the operation of the apparatus. The operation of the apparatus, therefore, had to be stopped after about one month's operation of the apparatus. When the pipes and the devices were opened and inspected, a sign of adhesion of scale was detected.

Example 8

The apparatus for the production of acrylic acid illustrated in FIG. 1 was used and the discharged gas was recycled to the reactor ① by following the procedure of Example 2 while using a gravity separation type mist separator capable of absorbing mist particles of a minimum diameter of 800 $\mu$m for separation of a mist from the discharged gas before elevation of the gas temperature.

When the circulation gas line was inspected after one month's continued operation of the apparatus, few adhering deposit was detected. When the compressor was inspected after one year's continued operation of the apparatus, absolutely no sign of corrosion or blockage was detected.

The column bottom liquid obtained in the absorption column ② was supplied through the lines 8 and 10 to the purification column not shown in the diagram. Incidentally, the column bottom liquid had the same composition as in Example 1. When the interior of the purification column was inspected after one year's continued operation of the apparatus, absolute no sign of corrosion or blockage was detected.

What is claimed is:

1. In a process for the production of (meth)acrylic acid comprising at least a step for the reaction of (meth)acrylic acid by catalytic gas phase oxidation and a step for the absorption thereof, a method for preventing an effluent gas pipe from blocking, characterized by causing part or the whole of the gas discharged from said step for absorption, while being circulated via said effluent gas pipe to said step for the reaction or being discarded, to be maintained at the same temperature as the temperature of said waste gas from said step for absorption or to be elevated to a temperature higher than the temperature of said waste gas from said step for absorption.

2. A method according to claim 1, wherein said discharged gas is further compressed.

3. A method according to claim 1, wherein the discharged gas outlet temperature at said step for absorption is in the range of 30–70° C.

4. A method according to claim 1, wherein said elevation of temperature is in the range of higher than 0° C. and not higher than 50° C.

5. A method according to claim 1, wherein the linear velocity of said discharged gas is in the range of 5–40 m/s.

6. A method according to claim 4, wherein said elevation of temperature is attained by elevating the temperature of said discharged gas by the use of a heat exchanger.

7. A method according to claim 6, wherein said heat exchanger is a finned-tube type or a plate type.

8. A method according to claim 1, wherein the separation for removal of mist is carried out before and/or after performing said temperature elevation.

9. A method according to claim 8, wherein said separation for removal of the mist is carried out by the use of a gravity separation type, centrifugal separation type, or a collision type mist separator capable of absorbing mist particles of a minimum diameter of 100 μm.

10. In a process for the production of (meth)acrylic acid comprising at least a step for the reaction of (meth)acrylic acid by catalytic gas phase oxidation and a step for the absorption thereof, a method for preventing an effluent gas pipe from blocking, characterized by causing part or the whole of the gas discharged from said step of absorption, while being circulated via said effluent gas pipe to said step of reaction or being discarded, to be stripped of mist, wherein said separation for removal of the mist is carried out by the use of a gravity separation type, centrifugal separation type, or a collision type mist separator capable of absorbing mist particles of a minimum diameter of 100 μm.

11. A method according to claim 10, wherein said separation for removal of the mist is carried out by the use of a gravity separation type, centrifugal separation type, or a collision type mist separator capable of absorbing mist particles of a minimum diameter of 100 μm.

12. A method according to claim 10, wherein said discharged gas is further compressed.

13. A method according to claim 10, wherein the linear velocity of said discharged gas is in the range of 5–40 m/s.

14. In a process for the production of (meth)acrylic acid comprising at least a step for the reaction of catalytic gas phase oxidation of (meth)acrylic acid and a step for the absorption of the product of the reaction, a method for the production of (meth)acrylic acid, characterized by causing part or the whole of discharged gas having a gas outlet temperature in the range of 30–70° C. at said step for absorption, while being circulated through an effluent gas pipe to said step for reaction, to be either maintained at the same temperature as the temperature of said discharged gas from said step for absorption or elevated to a temperature higher than the temperature of said waste gas from said step for absorption.

15. A method according to claim 14, wherein said elevation of temperature is in the range of higher than 0° C. and not higher than 50° C. and the linear velocity of said discharged gas is in the range of 5–40 m/s.

16. A method according to claim 14, wherein the separation for removal of mist is carried out before and/or after performing said temperature elevation.

17. A method according to claim 16, wherein said separation for removal of the mist is carried out by the use of a gravity separation type, centrifugal separation type, or a collision type mist separator capable of absorbing mist particles of a minimum diameter of 100 μm.

* * * * *